United States Patent
Stahlecker et al.

(10) Patent No.: US 6,488,889 B1
(45) Date of Patent: Dec. 3, 2002

(54) PROCESS AND SYSTEM FOR EVACUATING A PLASMA STERILIZATION REACTOR

(75) Inventors: Werner Stahlecker, Göppingen (DE); Robert Frost, Landshut (DE)

(73) Assignee: Rudiger Haaga GmbH, Altoberndorf (DE)

( * ) Notice: Subject to any disclaimer, the term of this patent is extended or adjusted under 35 U.S.C. 154(b) by 0 days.

(21) Appl. No.: 09/548,654

(22) Filed: Apr. 13, 2000

(30) Foreign Application Priority Data

Apr. 13, 1999 (DE) .......................... 199 16 478

(51) Int. Cl.⁷ .................................. A61L 2/00
(52) U.S. Cl. .................. 422/22; 250/455.11; 422/23; 422/33; 422/186.05
(58) Field of Search ............... 422/22, 23, 33, 422/186.05, 295; 250/455.11

(56) References Cited

U.S. PATENT DOCUMENTS

| | | | | |
|---|---|---|---|---|
| 3,701,628 A | | 10/1972 | Ashman et al. ............. 21/54 R |
| 3,948,601 A | * | 4/1976 | Fraser et al. ................. 422/23 |
| 5,656,238 A | * | 8/1997 | Spencer et al. ........ 422/186.05 |
| 5,904,866 A | * | 5/1999 | Kasper ................. 219/121.43 |
| 6,037,562 A | * | 3/2000 | Awakowicz et al. ... 219/121.48 |
| 6,162,405 A | * | 12/2000 | Awakowicz et al. ... 422/186.05 |
| 6,230,472 B1 | * | 5/2001 | Stahlecker ................. 53/331.5 |

* cited by examiner

Primary Examiner—Krisanne Thornton
(74) Attorney, Agent, or Firm—Crowell & Moring LLP

(57) ABSTRACT

A process is described for evacuating a reactor, in which at least one object is sterilized by means of Low pressure plasma. The reactor must be evacuated from atmospheric pressure to plasma discharge pressure. At least two separate, successive evacuation stages are hereby provided. In the first. evacuating stage and a possible further evacuation stage, the reactor is brought down step by step to a reduced intermediary pressure. In the last evacuation stage the reactor is evacuated to the plasma discharge pressure. For each evacuation stage it is advantageous to provide a separate vacuum chamber, to each of which the reactor is corrected. This brings with it the advantage that the entire amount of gas does not need to be transported through one single pump or a single set of pumps.

7 Claims, 2 Drawing Sheets

PROCESS AND SYSTEM FOR EVACUATING A PLASMA STERILIZATION REACTOR

BACKGROUND AND SUMMARY OF THE INVENTION

This application claims the priority of German application 199 16 478.9, filed in Germany on Apr. 13, 1999, the disclosure of which is expressly incorporated by reference herein.

The present invention relates to a process and system for evacuating a reactor, in which process at least one object is sterilized by means of low pressure plasma, from atmospheric pressure to plasma discharge pressure.

Reactors of this type are prior art in, for example, U.S. Pat. No. 3,701,628. Here it can be necessary to evacuate the reactor to pressures which lie in the range of fractions of a millibar.

The sterilizing effect of a plasma is based on its mechanical destruction of the bacteria by means of ion bombardment as well as on the chemical destruction by means of the occcurring radicals. Using only low energy requirements, the plasma can penetrate into the smallest surface cracks and holes, whereby with increasing vacuum the temperature can be reduced to such a low point that even heat sensitive objects, for example bottles made of plastic, can be processed.

In the case of sterilizing for example the inner surface of containers, the container inner pressure must, before the plasma phase begins, be reduced from atmospheric pressure (1000 mb) to plasma discharge pressure (for example 0.2 mb) If in the case of an industrial installation, a plurality of containers, and thus reactors, are to be evacuated within the shortest possible time, then volumes of gas, which can easily reach thousands of liters per second at the level of the plasma discharge pressure, must be pumped out. This leads to huge practical problems.

It is an object of the present invention to pump out, even at the lowest plasma discharge pressures, large amounts of gas in evacuable reactors cost-effectively and easily.

This object has been achieved in accordance with the present invention in that two successive but separate evacuating stages are provided, whereby the reactor is evacuated in the first evacuation stage to an intermediary pressure and at least to the plasma discharge pressure in the last evacuation stage.

Thus, instead of a one-stage evacuation, a so-called differential evacuation takes place. Vacuum pumps can be applied for each evacuation stage, said pumps being particularly efficient for the relevant pressure range. The individual pumps are activated parallel to one another, so that they deliver different mass flow. By means thereof, most of the gas volume to be pumped, for example 97%, is pumped out during the first evacuation stage, so that this amount is guided past at the second and at a possible third evacuation stage, which then function at a low pressure level. This saves the latter mentioned pumps—from the viewpoint of its pressure level—from having to handle huge volumes of gas. It should be mentioned here, that in the case of a gas expanding to an increasingly smaller pressure, the volume of the gas increases by the relevant factor.

A separate vacuum chamber is advantageously provided for every evacuation stage, to which the reactor is respectively connected. For example, three vacuum chambers can be provided which work at different pressure levels.

The following is an example:

In a first evacuation stage, the respective reactor can be pumped from atmospheric pressure to an intermediary pressure of 30 mb. In a further evacuation stage, the pressure level is brought down to 1.3 mb. In the subsequent third and last evacuation stage, the plasma discharge pressure of, for example, 0.2 mb is reached. By means of this differential evacuation, only a few hundred liters of gas volume per second is pumped off per evacuation stage. Without this differential pumping, the pump would have to transport several thousand liters of gas per second.

This pressure level reached in the last evacuation stage is maintained until the end of the serialization process, that is, during the entire plasma phase.

In the case of an arrangement for carrying out the process, a plurality of reactors can be provided, which are each provided with devices for taking up at least one container to be sterilized and to which at least two vacuum chambers of differing pressure levels are arranged, to which the reactors can be connected successively by means of valves or the like. For example, every 0.2 seconds a container to be sterilized can be delivered, whose inner pressure must be brought to the relevant plasma discharge pressure. The individual pumps are thus not directly connected with the reactors to be evacuated, but rather are connected continuously to the vacuum chambers, to which in turn the reactors to be evacuated are connected successively. Thus the time available for evacuating to the plasma discharge pressure is longer than the tact time in which the individual containers are fed.

In an embodiment of the present invention, the reactors are arranged on the periphery of a rotary runner, which runs through a plurality of stationarily arranged sectors, to each of which a vacuum chamber of differing pressure levels is arranged. The vacuum chambers are hereby in the form of ring channels which rotate with the rotary runners.

These and further objects, features and advantages of the present invention will become more readily apparent from the following detailed description thereof when taken in conjunction with the accompanying drawings.

DETAILED DESCRIPTION OF THE DRAWINGS

Figure 1:
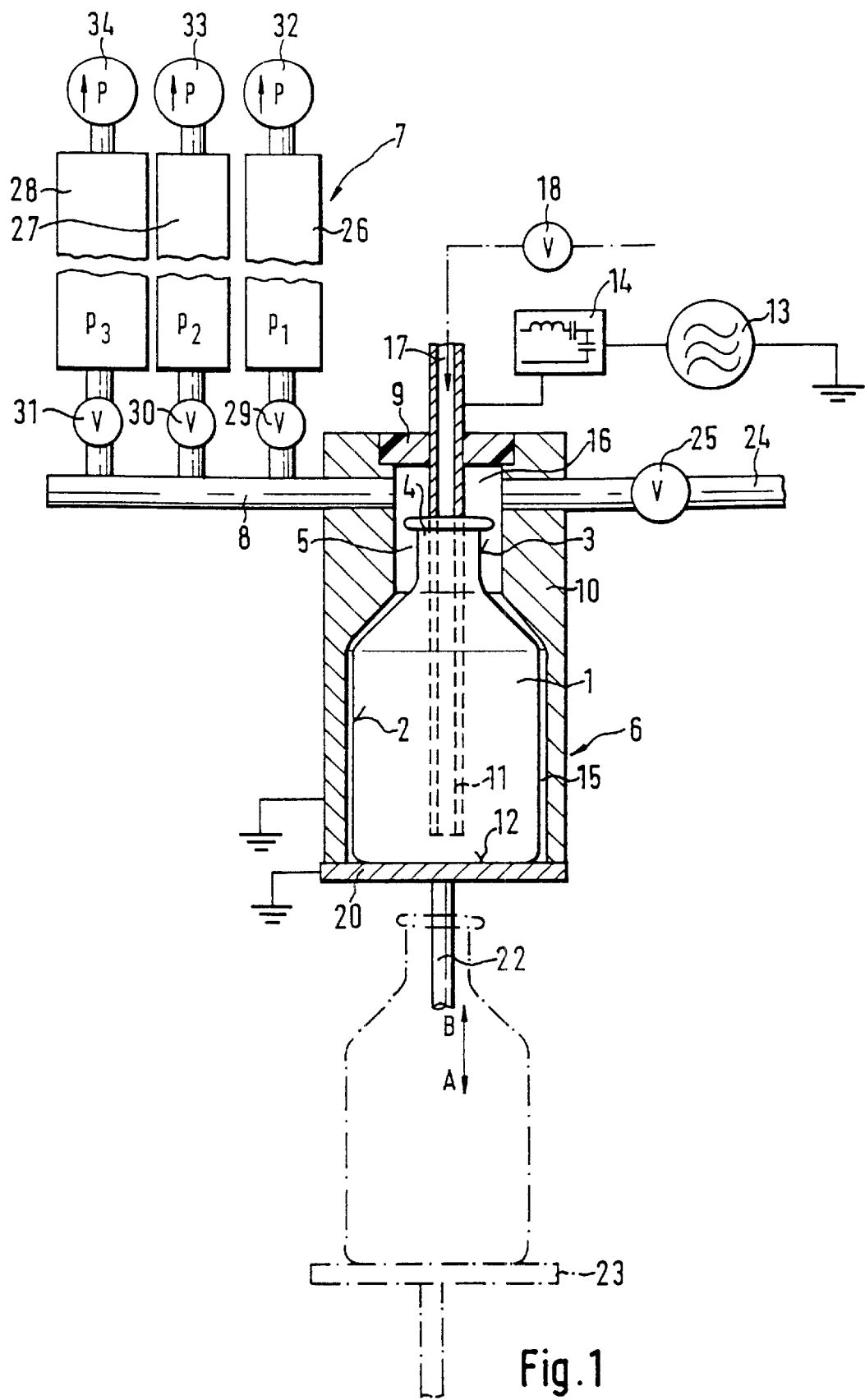
FIG. 1 is a partly sectional schematic view of a sterilizing device comprising a reactor, in which a container is sterilized by means of low pressure plasma, and constructed according to a preferred embodiment of the invention.

The sterilizing device shown in FIG. 1 serves the sterilizing of containers 1 by means of low pressure plasma and thus low temperatures. In the case of these containers 1, which are pressure sensitive and electrically non-conductive, the inner surfaces 2 in particular are to be made free of bacteria. Of the outer surfaces 3 in contrast, only those which are located in the area of the filling opening 4 need be sterilized, namely a transport collar and a thread for a lid which is applied at a later stage to the container 1. For the sterilizing process, a container 1 is taken up in a chamber 5 of an evacuable reactor 6, which is connected to an evacuating device 7. The chamber 5 as well as the container 1 are evacuated by means of a suction tube 8 entering the filling opening 4.

In order to generate the plasma, two electrodes 10 and 11 are provided, which are arranged coaxially to one another and insulated against one another by an insulation 9, of which electrodes the electrode 10 is the outer electrode and the electrode 11 is the inner electrode. The outer electrode 10 is earthed (grounded) and so designed that it forms a chamber 5 during operation which takes up the container 1 and surrounds it closely with a wall. This permits a vacuum to be located in the inside of the container 1 as well as outside the container 1, so that the container 1 does not need to be dimensionally stable. The inner electrode 11 can be inserted through the filling opening 4 and ends in close proximity to the container bottom 12.

A high frequency generator 13 serves to generate the alternating voltage, which delivers a power level using a permitted industrial frequency, for example 13.56 MHz or 27.12 MHz. Power is capacitively coupled in from an adapter network 14 by means of the inner electrode 11.

Because of the narrow gap 15 between the wall of the outer electrode 10 and the outer contour of the container 1, no plasma can be ignited outside of the container 1. This desirable state is given when the gap 15 measures only a few millimeters. The plasma is essentially only ignited in the inside of the container 1, so that essentially only the inner surface 2 of the container 1 is sterilized.

As in addition to the inner surface 2 also a part of the outer surface 3 in the area of the filling opening 4 is also to be sterilized, the outer electrode 10 comprises in this area a recess 16 in such a way that the outer electrode 10 has clearance in relation to the outer surface 3. Thus the ignited plasma can also reach the transport collar and the thread.

The inner electrode 11 comprises a supply line 17 for a process gas to be ionized. The process gas is let into the container 1 and thus into the chamber 5 by means of a valve 18. The pressure can be checked by means of a pressure gaging device (not shown). The most suited plasma discharge pressure depends on the type of gas used and can lie in the range of 0.1 Pa to several hundred Pa. A particularly suitable process gas is, for example, hydrogen peroxide, but other gases can also be used.

When the chamber 5 is closed, the container 1 stands with its bottom 12 on the bottom 20 of the reactor 6. The bottom 20 comprises a conducting and also earthed (grounded) base plate and can thus continue the outer electrode 10 during operation. The bottom 20 is also formed corresponding to the container bottom 12, so that here also no plasma is ignited outside of the container 1.

The bottom 20 is applied to a lifting rod 22 movable according to the directions of motion A and B, so that the chamber 5 can be opened and closed for feeding and removing the container 1. The lowered position of the bottom 20 is denoted by a dot-dash line and numeral 23.

A supply line 24 for a sterile flooding gas for after the completion of the sterilizing process enters the area of the filling opening 4. The supply line 24 comprises a valve 25.

Due to the coaxial positioning of the inner electrode 11 to the outer electrode 10, the power sourcing is axially symmetric and thus very homogenous. The grounded outer electrode 10 forms, together with the also grounded bottom 20, an ideal high frequency shielding of the reactor 6. Only the inner electrode 11 projecting out of the chamber 5 and the adapter network 14 to be applied directly to this area require an additional shielding.

As the supply line 17 for the process gas is arranged in the inside of the inner electrode 11, the inside of the container 1 can be flooded with the process gas quickly and easily, whereby the remaining rest air is at the same time displaced. This can take place at the level of the process pressure, so that it is not necessary to evacuate the chamber S under discharge pressure. By maintaining a stationary process gas flow during the plasma phase, a reproducable process course is guaranteed.

The inner electrode 11 can serve additionally as a filling tube. Advantageously, a hollow tappet can be used for feeding the process gas, while the outer ring-shaped cross section surface is available for the filling contents.

The process takes place as follows: First the container 1, standing on the bottom 20 of the reactor 6, is pushed into the chamber 5 from below. The bottom 20 is pressed hereby against the outer electrode 10 and the chamber 5 is closed by means of an intermediary seal.

Subsequently the chamber 5 together with the container 1 is evacuated by means of the evacuating device 7, namely to the level of plasma discharge pressure. During this phase, only rest air fills the chamber 5.

Next, process gas is fed by means of the supply line 17 located in the inside of the inner electrode 11, whereby the rest air is displaced from below upwards out of the container 1 and is suctioned off in the head area of the reactor 6. This flow of process gas can, if required at a reduced flow, be maintained after the now subsequent plasma ignition until the end of the plasma phase. This maintained flow during the plasma phase ensures in a technically simple way that the desired conditions prevail and that the maximum process gas concentration in the inside of the container 1 is ensured.

After completion of the plasma serialization and after the flow of the process gas has been switched off, flood gas is now flooded, for example with sterile air or with sterile inert gas. The preferred choice would be, for example, nitrogen. The flood gas is brought into the headroom of the reactor 6 by means of a supply line 24. If the process pressure measures, for example, 20 to 50 Pa, a concentration dilution, to a factor of 2000 to 5000, of the process gas still located in the container 1 is achieved when flooding takes place at normal pressure. If hydrogen peroxide is used as a process gas, essentially only water and molecular oxygen remain after the plasma switch-off.

If the container 1 is in addition filled in the reactor 6, advance flooding with nitrogen at a pressure of possibly clearly over one bar, that is by means of a bias pressure with sterile nitrogen, foaming of the filling contents can be reduced or possibly completely prevented, which permits filling to take place faster.

A device (not shown) for closing the container 1 is applied for this purpose below the reactor 6. As soon as the container 1 is pulled downwards out of the chamber 1, the container 1 can be closed by means of a seal.

As mentioned above, the reactor 6, that is, its chamber 5 has to be evacuated from atmospheric pressure to plasma-discharge pressure, for example 0.2 mb. In the case of an industrial installation, this step must be repeated in fractions of a second, because of the large numbers of containers 1 to be sterilized. If, for example, a new container 1 is fed every 0.2 seconds, one liter of air, for example, must be evacuated at a pressure of 1000 mb every 0.2 seconds. At the pressure level of the plasma discharge pressure, this would correspond to a volume of 5000 liters. The volume of gas to be pumped per second would be 25,000 liters, which would lead to technically unsolvable problems. For this reason, in the example in FIG. 1, three successive, but separate, evacuating stages are provided, whereby a vacuum chamber 26,27,28 is arranged at each respective evacuating stage.

These vacuum chambers 26,27 and 28, which can be designed as closed circular pipe lines, each have a different pressure level $P_1$, $P_2$ and $p_3$. The first vacuum chamber 26 has c pressure level of 30 mb, for example, whereas the second vacuum chamber 27 can have a pressure level of, for example, 1.3 mb. The third vacuum chamber 28 leads then to the plasma discharge pressure, for example 0.2 mb. The vacuum chambers 25,26,27 are connected to the reactor 6 one after the other, but separately from one another, by means of valves 29,30 and 31. The pumps 32,33 and 34 belonging to the vacuum chambers 25,26 and 27 respectively, do not function, as is usual, in series, but rather are connected parallel. In this way, great pressure differences can be achieved by means of differential evacuation, whereby only a few hundred liters are pumped per pump 32,33 and 34 per second.

The pump 32 arranged at the first evacuation stage pumps the largest percentage of the gas volume, for example, 97%. This large gas volume does not need to be pumped by the pumps 33 and 34 of the next two evacuation stages, so that the pumps 33 and 34 can function very effectively at a low pressure level. The pressure level of the last evacuation stage remains connected to the reactor 6 until the plasma phase is completed.

Figure 2:
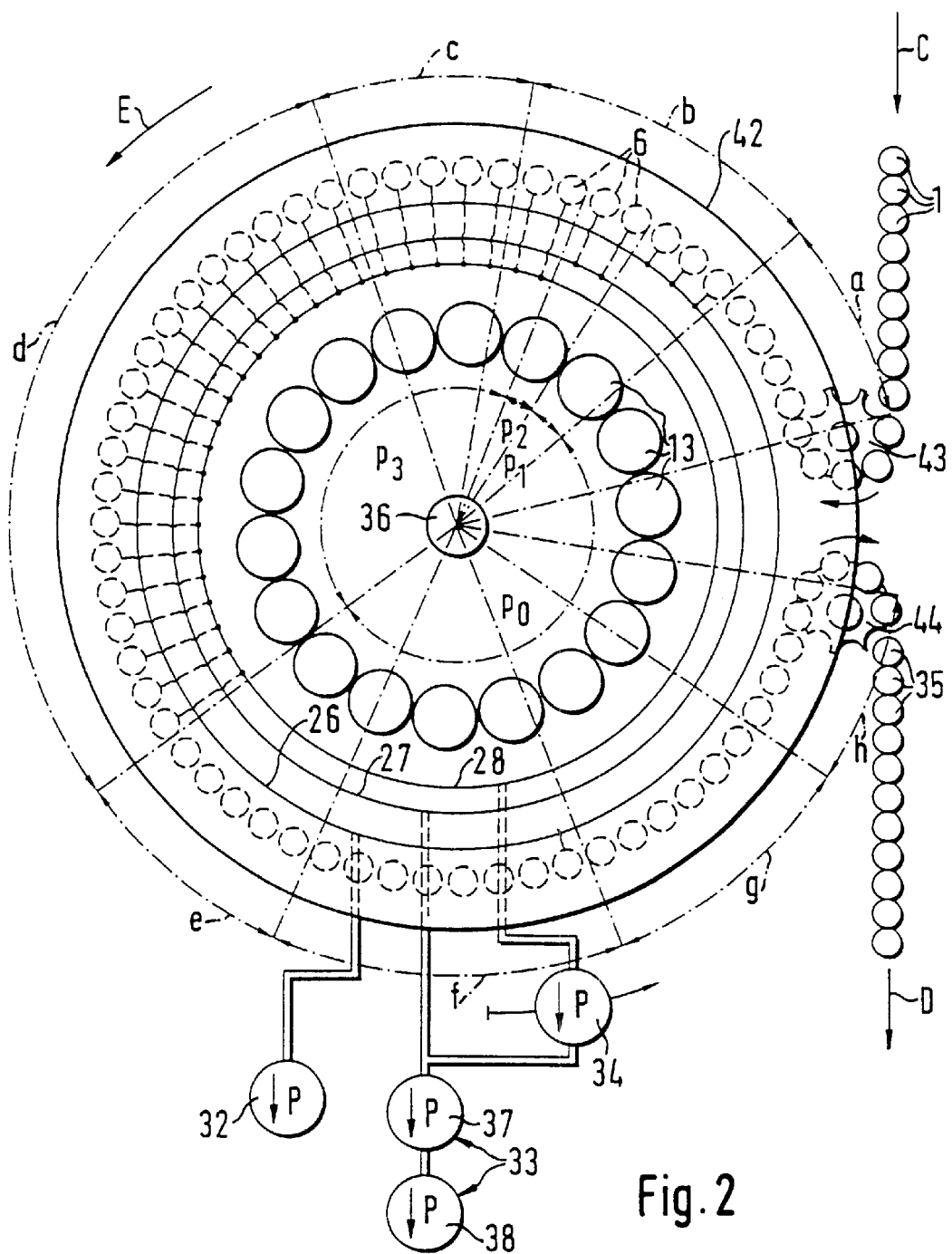
FIG. 2 is, in highly schematic representation, a top view onto a rotary runner comprising a plurality of reactors, constructed according to a preferred embodiment of the invention.

According to the very schematically shown FIG. 2, a plurality of reactors 6 can be arranged at the periphery of a round runner 42. For example, one hundred of these reactors 6 could be provided. Each of these reactors 6, as described above wish the aid of FIG. 1, takes up a container 1 to be sterilized. These containers 1 are, for example, fed by means of a transport device (not shown) in feed direction C to the round runner 42. The containers 1 successively reach the area below the reactors 6 by means of a feed star 43, which rotates in arrow direction, said containers L then being placed in the reactors 6 in the way described above. Accordingly there is a rotating exit star 44 which rotates in arrow direction, by means of which the sterilized, possibly filled and closed containers 35 are transported away in removal direction D.

If the round runner 42 comprises for example 50 reactors, and is fed a container every 0.2 seconds, then the rotation time takes 10 seconds. Capacity lies then in the order of magnitude of 20,000 containers 1 per hour.

The round runner 42 is driven around an axle 35 in travel direction E. The individual reactors 6 travel through so-called sectors, which are stationarily arranged to the round runner 42 and are denoted by a small letter and a double arrow. In each of these sectors a to h, a very specific procedural stage is carried out, whereby the individual reactors 6 travel one after the other through the individual sectors due to the rotational movement of the round runner 42.

In sector a, the containers 1 to be sterilized are fed to the round runner 42 and from there are pushed into the individual reactors 6 from below. The reactors 6 are hereby sealed closed against gas.

In sector b, the individual reactors 6 are evacuated in a way to be described in more detail below. In the following sector c a process preparation takes place, whereby essentially the chamber 5 and the inside of the container 1 are flooded with process gas. In the following sector d, the actual plasma serialization takes place. In sector e the respective reactor 6 is flooded in a sterile way with flood gas to normal pressure.

Before the sterilized containers 1 are transported further, it is possible that two further sectors f and g are provided. In sector f, the sterilized containers 1 are filled preferably with filling contents, while in sector g they are subsequently sealed closed in a sterile way. The sterilized, filled and closed containers 35 can then be ejected from the round runner 42 in the adjoining sector h and subsequently transported away in transport direction D.

The high frequency generators 13 described above with the aid of FIG. 1 are also mounted on the round runner 42. As the sector d which serves the actual serialization takes up only a part of the periphery of the round runner 42, it is sufficient when a plurality of reactors 6 are arranged at one high frequency generator 13. For example, as shown in FIG. 2, three reactors 6 can be arranged for one high frequency generator 13. The placing is so arranged that one high frequency generator 13 connected to a reactor 6 remains connected during the entire passage through the sector d, that this high frequency generator 13 is disconnected when it reaches the sector e and subsequently is connected to another reactor 6, which has not yet reached the sector d. A relay connection (not shown) is provided for this purpose. Thus, at any one time, a specific reactor 6 is run by a specific high frequency generator 13. It is provided, in contrast, that each reactor 6 has its own adapter network 14 arranged in direct proximity to it.

As mentioned above, the evacuation of the individual reactors 6 takes place in sector b, namely in the present case in three separate, successive evacuation stages. A vacuum chamber 26,27,28, designed as a closed circular pipe line, is arranged at each of the three evacuation stages, which vacuum chambers 26,27 and 28 are positioned on the round runner 42. Each of these vacuum chambers 26,27 and 28 represents a certain pressure level $P_1$, $P_2$ and $p_3$ The area of these three pressure levels $P_1$, $P_2$ and $p_3$ are denoted in the vacuum chambers 26,27 and 28 in FIG. 1 as well as a sector in FIG. 2. Here the large sector can also be seen to which the atmospheric pressure $p_0$ is given.

As can be seen in FIG. 2, the differential evacuation begins at the first part of the sector b, whereby three reactors 6, one after the other, are first connected to the vacuum chamber 26 designed as a closed circular pipe line. Downstream, still in sector b, two reactors 6 are connected to the vacuum charmer 27 having an already reduced pressure level. At the end of the sector b, two reactors 6 are connected to the third vacuum chamber 28, whose pressure level is already that of the plasma discharge pressure. This plasma discharge pressure is maintained until the end of the plasma phase, that is until the end of the sector d. The pressure $p_3$ corresponds thus to the plasma discharge pressure.

Due to this differential evacuation, pumps 32,33 and 34 of a type operating most efficiently in their respective pressure range, can accordingly be used for each different evacuation stage.

In the case of the pump 32 of the first evacuation stage, for example, a sliding vane rotary pump can be involved, which operates optimally at pressures of above one millibar. In the case of the pump 33 of the following evacuation stage, for example, a set of pumps can be involved, which consists of two pumps 37 and 38 connected in series one behind the other. The pump 37 is hereby a Roots vacuum pump, while in the case of the pump 38, a backing pump in the form of a sliding vane rotary pump is provided. This is because Roots pumps cannot function against the atmospheric pressure and require therefore a backing pump which sucks at the exhaust of the Roots pump and condenses the gas transported by the Roots pump and expels it against the atmospheric pressure. In the case of the third pump 34, which is connected to the plasma discharge pressure of the last evacuation stage, a Roots pump is again involved here. To this pump 34 the Roots pump 37 mentioned above can be arranged as a backing pump.

The flow resistance of the respective pipe lines are strongly dependent on pressure. In the case of the differential evacuation according to the present invention, it is now possible to arrange the cross sections of the individual supply lines optimally to the individual pressure levels and co adapt them to the volume flow to be transported. For the first evacuation stage, a large supply line cross section is required, as a large volume of gas must flow through here. In the next evacuation stage, which lies in the order of magnitude of one millibar, a relatively small volume of gas flows, and the flow resistance is also relatively low at this pressure. Here a smaller cross section is sufficient. For the level of the plasma discharge pressure, a large cross section is required again; although the volume of gas to be transported is relatively low, the flow resistance at such a low pressure of only 0.2 mb is relatively high.

As indicated in FIG. 2, the pumps 32 and 33 are positioned stationarily at the installation, while the pump 34 connected to the plasma discharge pressure is positioned directly on the round runner 42, as the supply line should be kept as short as possible in order to minimize the flow of resistance.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An arrangement for carrying out a process for evacuating a reactor, in which process at least one object is sterilized by low pressure plasma, from atmospheric pressure to plasma discharge pressure, wherein at least two successive, but separate, evacuation stages are provided, whereby the reactor in the first evacuation stage is evacuated to an intermediary pressure and in the last evacuation stage the reactor is evacuated at least to the plasma discharge pressure, said arrangement comprising:

a plurality of reactors which are each provided with devices for taking up at least one of the containers to be sterilized and to which at least two vacuum chambers of differing pressure levels are arranged, and to which the reactors are successively connectable, wherein the reactors are arranged at the periphery of a round runner, which travels through a plurality of stationarily arranged sectors, at each of which a sector vacuum chamber of differing pressure levels is arranged.

2. An arrangement according to claim 1, wherein the vacuum chambers are designed as closed circular pipe lines.

3. An arrangement according to claim 1, wherein at least one pump is arranged at each vacuum chamber, whereby the pump related to the plasma discharge pressure is arranged on the round runner.

4. An arrangement according to claim 2, wherein at least one pump is arranged at each vacuum chamber, whereby the pump related to the plasma discharge pressure is arranged on the round runner.

5. A system for sterilizing inner surfaces of containers comprising:

a plurality of reactors having respective container holding chambers, said reactors forming one electrode of a plasma generator, a second electrode disposable in a container held in the container holding chamber of a respective reactor, a high frequency generator operable to supply alternating voltage to the one electrode, and an evacuation assembly operable to evacuate the container holding chambers, said evacuation assembly including a plurality of vacuum chambers at different vacuum pressure levels and means for successively connecting the vacuum chambers with a respective container holding chamber, wherein the reactors are arranged at the periphery of a round runner, which travels through a plurality of stationarily arranged sectors, at each of which a sector vacuum chamber of differing pressure levels is arranged.

6. A system according to claim 5, wherein the vacuum chambers are designed as closed circular pipe lines.

7. A system according to claim 6, wherein at least one pump is arranged at each vacuum chamber, whereby the pump related to the plasma discharge pressure is arranged on the round runner.

* * * * *